United States Patent
Liard

(10) Patent No.: US 11,491,101 B2
(45) Date of Patent: Nov. 8, 2022

(54) COMPOSITION FOR STRIP-FREE HAIR REMOVAL

(71) Applicant: S.A. THALGO TCH, Roquebrune-sur-Argens (FR)

(72) Inventor: Alexis Liard, Neuilly Sur Seine (FR)

(73) Assignee: S.A. THALGO TCH, Roquebrune-sur-Argens (FR)

( * ) Notice: Subject to any disclaimer, the term of this patent is extended or adjusted under 35 U.S.C. 154(b) by 181 days.

(21) Appl. No.: 16/315,777

(22) PCT Filed: Jul. 6, 2017

(86) PCT No.: PCT/FR2017/051844
§ 371 (c)(1),
(2) Date: Jan. 7, 2019

(87) PCT Pub. No.: WO2018/007760
PCT Pub. Date: Jan. 11, 2018

(65) Prior Publication Data
US 2019/0142728 A1 May 16, 2019

(30) Foreign Application Priority Data

Jul. 7, 2016 (FR) ..................................... 16 56 555

(51) Int. Cl.
| | | |
|---|---|---|
| A61K 8/81 | (2006.01) | |
| A61Q 9/04 | (2006.01) | |
| A61K 8/92 | (2006.01) | |
| A61K 8/31 | (2006.01) | |

(52) U.S. Cl.
CPC .............. *A61K 8/8135* (2013.01); *A61K 8/31* (2013.01); *A61K 8/8111* (2013.01); *A61K 8/8117* (2013.01); *A61K 8/92* (2013.01); *A61Q 9/04* (2013.01); *A61K 2800/54* (2013.01); *A61K 2800/805* (2013.01)

(58) Field of Classification Search
CPC ...... A61K 8/8135; A61K 8/31; A61K 8/8111; A61K 8/8117; A61K 8/92; A61K 2800/54; A61K 2800/805; A61Q 9/04
See application file for complete search history.

(56) References Cited

U.S. PATENT DOCUMENTS

| | | | |
|---|---|---|---|
| 4,282,877 A | * | 8/1981 | Mathews |
| 2008/0021149 A1 | * | 1/2008 | Jones |
| 2010/0256274 A1 | | 10/2010 | Heemann |
| 2012/0259050 A1 | * | 10/2012 | Vitrano |
| 2013/0150867 A1 | | 6/2013 | Atteia |
| 2016/0046736 A1 | | 2/2016 | Brindle |

FOREIGN PATENT DOCUMENTS

| | | |
|---|---|---|
| FR | 2577134 A1 | 8/1986 |
| FR | 2617708 A1 | 1/1989 |
| FR | 2637498 A1 | 4/1990 |
| FR | 2751872 A1 | 2/1998 |
| FR | 2751873 A1 | 2/1998 |
| FR | 2940070 A1 | 6/2010 |
| WO | 3828015 A1 | 7/1998 |
| WO | 2008103817 A1 | 8/2008 |

OTHER PUBLICATIONS

Dow Safety Data Sheet for Affinity GA 1900 (pp. 1-11, accessed on Jan. 15, 2021 from https://www.dow.com/en-us/document-viewer.html?docType=SDS&contentType=SDS&product=17531z&tradeProduct=000000017531&selectedCountry=US&selectedLanguage=EN&recordNumber=27805129 (Year: 2021).*
Database GNPD (Online) MINTEL:, Jul. 2009, "No Strip Wax", XP002764538.
International Search Report for corresponding application PCT/FR2017/051844 filed Jul. 6, 2017; dated Aug. 30, 2017.

* cited by examiner

*Primary Examiner* — Alma Pipic
(74) *Attorney, Agent, or Firm* — Cantor Colburn LLP

(57) ABSTRACT

The invention relates to an adhesive composition having a main fraction of synthetic tackifying resin, and a fraction of at least one macromolecular component, characterised in that said at least one macromolecular component comprises a copolymer of at least two different monomers taken from the alpha olefins and ethylene, to give the composition for strip-free hair removal mechanical or adhesive properties.

14 Claims, No Drawings

COMPOSITION FOR STRIP-FREE HAIR REMOVAL

TECHNICAL BACKGROUND

The invention related to the field of hair removal compositions especially for human use and, in particular but not limited to, professional use.

There are known compositions based essentially on rosin, which is a solid residue coming from the distillation of products from coniferous trees, in particular pine. Rosin is a resin with a tackifying property (i.e. having adhesion properties). Rosin is the largest fraction of these compositions and is mixed with only small fractions of fatty products such as oils or lanolin and waxes. Before their application, these compositions have to be heated for a long time before becoming sufficiently soft to be applied to the skin. In certain situations, the temperature obtained is too high, which is dangerous or unpleasant for the person to be depilated. Furthermore, the thickness of the composition to be applied is necessarily significant (5 mm for example), because of the low mechanical strength of the composition once it is spread. However, these compositions are reusable after filtration.

Also known are compositions that still contain rosin, but also comprise oils in higher proportions than in the previous example, and optionally comprise sugars or waxes with a suitable softening point (softening at a lower temperature than the previous compositions), and which require less heating. These compositions, however, require the use of a support film (paper or cotton/cellulosic or plastic strip, such as cellophane film) in order to remove them once they are applied to the skin as they also suffer from the low mechanical strength of the composition. These compositions are not reusable, and are discarded after use. Compositions of this type are known, for example, from document FR2577134. Other compositions of this type using a synthetic resin in the place of rosin are also known from WO2008/103817. Synthetic resins are described later in this text.

In this context, the invention relates more specifically to a hair removal composition for removing hairs that do not require a strip of paper or plastic to be applied. This composition has mechanical properties which are such that the use of such a strip becomes unnecessary. Nevertheless, it may be deposited in a thin layer.

Compositions of this type are known, for example, from the documents FR2617708, FR2637498, FR2751872 and FR2751873.

In general, such compositions contain, first of all, a resin with a tackifying property and a macromolecular compound providing mechanical properties. Other constituents are present in the composition, such as, in particular, softeners or emollients, such as waxes or oils.

The resin with a tackifying property is often a rosin, i.e. as mentioned above, a resin of natural origin. The molecules of rosin have oxygen atoms and have a certain polarity. It may be unmodified rosin (acid) or modified through hydrogenation, esterification, or dimerization. Alternatively, a synthetic resin, derived from petroleum products, may be used. This is a set of carbon molecules generally less polar than rosin. Synthetic resins known as C5 (copolymers based on diene monomers—aliphatics—such as pentadiene, methylbutene, dicyclopentadiene, cyclopentadiene and cyclopentene) are known, most often cyclopentadiene, and synthetic resins called C9 (copolymers based on aromatic monomers such as vinyltoluene, dicyclopentadiene, indene, methylstyrene, styrene and methylindene), most often a styrene/methylstyrene/indene copolymer. These resins exist in various grades and may also be modified, in particular, by hydrogenation.

The resin, natural or synthetic, is generally the compound that is present in the largest proportions, by weight, in the composition.

The macromolecular component providing mechanical properties may be a wax, i.e. a fatty acid ester. It is generally present in proportions by weight that are lower than those of the resin. There are animal, vegetable or mineral waxes that may be used, one example being beeswax. In particular, they have a certain plastic behavior. The macromolecular component may also be an elastomer, often cheaper, and which may have better mechanical properties, particularly in terms of tensile strength and flexibility or suppleness due to the absence of vitreous behavior in the temperature range used. The introduction of these elastomers by mixing in the resin which has an initially vitreous behavior, makes it possible to provide an amorphous tendency. It may, in particular, be a natural rubber or a synthetic polymer or copolymer such as an ethylene/vinyl acetate (EVA) copolymer.

Compositions of this class also include softeners and emollients, such as fats, oils or waxes, which also participate in the rheological regulation and modulation of the solidification time. These compositions are used following heating to its softening temperature for example around 55° C., and then by applying the composition on the parts of the body to be depilated at a temperature that is adapted to the comfort of the person to be depilated, who, obviously, should not feel too high a temperature.

The compositions mentioned above may be deposited in the form of fairly thin layers, and then removed by peeling, after a short time of solidification and cooling, to allow the removal of the hair.

The compositions are appreciated by people undergoing hair removal (for example, beauty salon clients) as well as by people practicing hair removal (e.g. beauticians of beauty salons). The criteria that cause a composition to be appreciated include its ability to remove hair (also called "pulling ability"), its absence of breakage (also called "mechanical properties") when manipulated as a layer, or the temperature felt upon the skin. Some users may give more value to certain criteria, so it is useful to have a variety of different compositions.

Despite the presence on the market of various products, there is room for improvement in offering users solutions that satisfy all of their requirements and according to their preferences, or that simply allow them to change products while retaining satisfactory properties. Moreover, until now elastomers were compounds that were only used for their mechanical properties (flexibility and tensile strength) but little for their adhesion potential. This resulted in a possibility of seeking an increase in the adhesion capacities by development of the compositions.

It was therefore been decided to launch new research in the field.

Definition of the Invention

To answer this problem, an adhesive composition is proposed comprising a main fraction of synthetic tackifying resin and a fraction of at least one macromolecular component, wherein the at least one macromolecular component comprises a copolymer of at least two different monomers taken from the group comprising alpha-olefins having at least 4 or at least 5 carbon atoms and ethylene (ethylene is not, in the context of the present text considered to be an alpha-olefin) for modulating adhesion properties and the mechanical strength of the composition for hair removal without a strip.

According to various advantageous but optional features:
the copolymer is an ethylene copolymer;
the copolymer is a copolymer of two monomers;
the copolymer is a copolymer that is less polar than EVA;
the copolymer is a more dissipative (less elastic) material than EVA;
the copolymer is a plastomer;
the copolymer is a copolymer produced by catalysis with a metallocene;
the copolymer is a copolymer obtained by coordinative copolymerization;
the copolymer is an ethylene/alpha olefin copolymer;
the copolymer is an ethylene/alpha olefin copolymer, wherein the alpha-olefin has at least 4 or at least 5 carbons;
the copolymer is an ethylene/octene copolymer;
the copolymer is characterized by a melt index of more than 100 g/10 min (2.16 kg @ 190° C.), or more than 250 g/10 min (2.16 kg @ 190° C.);
the copolymer is characterized by a melt index of less than 800 g/10 min (2.16 kg @ 190° C.), or less than 580 g/10 min (2.16 kg @ 190° C.);
the copolymer is characterized by a density of between 0.86 and 0.91 g/cm$^3$, or between 0.868 and 0.897 g/cm$^3$, or between 0.870 and 0.880 g/cm$^3$;
the composition does not contain an ethylene/vinyl acetate copolymer, while the copolymer of at least two different monomers chosen from the alpha-olefins indicated and ethylene are present in the composition in the form of a fraction by weight of between 1 and 18% or 5 and 15%;
or, on the contrary, the composition additionally comprises ethylene/octene copolymers (or more generally in addition to copolymers including an alpha olefin, optionally with the characteristics indicated above relating to the number of carbons), a fraction of an ethylene/acetate copolymer vinyl, the copolymer of at least two different monomers taken from the alpha-olefins indicated, and wherein the ethylene and the ethylene vinyl acetate copolymer are present together in the composition in the form of a fraction by weight of between 1 and 18% or 5 and 15%;
the synthetic tackifying resin is, for example, of the cyclopentadiene (C5) type, for example hydrogenated;
the synthetic tackifying resin is present at a level of at least 50% by weight, or even more than 60% by weight, or more than 70% by weight.

The invention also relates to a hair removal method comprising the application of a layer of an adhesive composition comprising a main fraction of synthetic tackifying resin and a fraction of at least one macromolecular component, wherein the application is carried out while the composition is hot, then peeling the layer without the use of a strip once the composition has cooled, wherein the at least one macromolecular component comprises a copolymer of at least two different monomers taken from alpha-olefins of at least 4 or at least 5 carbon atoms, and ethylene to modulate the strength properties or adhesive properties of the composition.

DETAILED DESCRIPTION

A reference formula 1 is compared with a formula 2 in which the elastomer components (28% EVA copolymers of vinyl acetate) present in the formula 1, are replaced by an ethylene octene copolymer, wherein the octene is an alpha-olefin. A polycyclopentadiene synthetic tackifying resin is used.

| Formula 1 is shown in the table below: | |
| --- | --- |
| Hydrogenated C5 resin | Majority component (>50%) |
| Synthetic waxes | Of the order of 10 to 20% |
| EVA (28% VA) (two different compounds) | Total EVA: of the order of 10%, between 5 and 15% |
| total | 100% |

Fractions are given by weight of the components based on the weight of the entire composition. This is also the case in the other formulas of this document.

| Formula 2 is shown in the table below: | |
| --- | --- |
| Hydrogenated C5 resin | As in formula 1 |
| Synthetic waxes | As in formula 1 |
| Ethylene/octene copolymer (Affinity GA 1950) | As much EVA as in Formula 1 Of the order of 10%, between 5 and 15% |
| total | 100% |

The Affinity GA 1950 ethylene/octene copolymer component is available from Dow Chemical. It is characterized by a melt index of 500 g/10 min (2.16 kg @ 190° C.) and a density of 0.874. It has a tensile strength of 1.76 MPa.

Other ethylene/octene copolymer grades may be used, for example with melt indices of more than 100 g/10 min (2.16 kg @ 190° C.), or more than 250 g/10 min (2.16 kg @ 190° C.)

The copolymer may also have a density of between 0.86 and 0.91 g/cm$^3$, 0.868 and 0.897 g/cm$^3$, or between 0.870 and 0.880 g/cm$^3$.

As an illustration, the two waxes used have the following characteristics: solidification point 58 to 80° C.

The resin is a hydrogenated C5 resin with a softening point between 85 and 100° C. and a molecular weight of 450 to 590 g/mol.

The EVA used for reference have melt indices of 100 and 500 g/10 min (2.16 kg @ 190° C.) respectively, and densities both of 950 kg/m$^3$. As already mentioned, this is EVA with 28% vinyl acetate.

These compositions were applied by hair removal specialists on persons to be depilated in the context of blind tests. The composition, initially in granules, is heated in a wax heater to form a warm paste. The heating is between 50° C. and 75° C., and preferably 58° C. to 68° C. Then the warm paste is applied, for example, with a wooden spatula to form a thin elongated layer of the composition that upon cooling, traps the hair or sticks them together and hardens.

This layer, once solidified by its spontaneous cooling is gripped at one of its ends and removed quickly in the opposite direction to the growth of the hair, through a qualified peeling operation. Peeling is thus performed between 20° C. and 38° C., often between 25° C. and 35° C.

Formula 2 has tearing properties and mechanical properties (no breakage), as well as olfactory properties of the product which are improved over formula 1.

The alpha-olefin used above is an alpha-olefin that is not a propylene. It has at least 4 or at least 5 carbons. It is an octene. The alpha-olefin used may also be, but is not limited to, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1 hexene, 1-octene, 1-decene, 1-dodecene, 1-tetradecene, 1-hexadecene, 1-octadecene or 1-eicosene, wherein each molecule is taken alone or possibly in combination, and is subject, of course, to the compatibility of the molecules aimed at cosmetic applications.

Of particular interest, although not a limitation of the invention, are copolymers of the plastomer type, having a more dissipative behavior than the EVA used hitherto.

The same tests were carried out with hydrogenated C9 resin compositions (aromatic tackifying resins).

The resin used is a hydrogenated C9 resin having a softening point between 85 and 100° C. and a molecular weight of 600 to 800 g/mol.

Formula 3 is shown in the table below. It is a formula with an ethylene vinyl acetate copolymer (EVA).

| | |
|---|---|
| Hydrogenated C9 resin | Majority component (>50%) |
| Synthetic waxes | Of the order of 10 to 20% |
| Beeswax | Between 5 and 10% |
| Paraffin oil | Between 1 and 3% |
| EVA (28% VA) (two different compounds) | Of the order of 10%, between 5 and 15% |
| Perfume | Low proportion (less than 2%) |
| total | 100% |

Formula 4 is shown in the table below. This is a formula with ethylene/octene copolymers

| | |
|---|---|
| Hydrogenated C9 resin | As in formula 3 |
| Synthetic waxes | As in formula 3 |
| Beeswax | As in formula 3 |
| Paraffin oil | As in formula 3 |
| Ethylene octene copolymer (Affinity GA 1950) | As EVA in formula 3 |
| Perfume | As in formula 3 |
| total | 100% |

The copolymers of ethylene octene lead to a composition which has properties at least as good as those of the composition comprising EVA. It is likely that improvement is possible if the formulas are modified while remaining within the scope of the invention in order to obtain an optimal result using ethylene octene copolymers.

Experiments were further conducted with the Affinity GA 1950 ethylene/octene copolymers mixed in the same composition with the EVAs according to the following formulas:

Formula 5:

| | |
|---|---|
| Hydrogenated C9 resin | Majority component (>50%) |
| Synthetic waxes | Of the order of 10 to 20% |
| Beeswax | Between 5 and 10% |
| Paraffin oil | Between 1 and 3% |
| Ethylene/octene copolymer (Affinity GA 1950) | Of the order of 6%, between 2 and 12% |
| EVA (28% VA) | Of the order of 4%, between 2 and 10% |
| Pigments | Low proportion (less than 2%) |
| Total | 100% |

Formula 6:

| | |
|---|---|
| Hydrogenated C5 resin | Majority component (>50%) |
| Synthetic waxes | Of the order of 10 to 20% |
| Ethylene/octene copolymer (Affinity GA 1950) | Of the order of 5%, between 2 and 12% |
| EVA (28% VA) | Of the order of 5%, between 2 and 12% |
| total | 100% |

The results showed an improvement of the tearing properties and the mechanical properties (absence of breakage), as well as a decrease in residues and odor, compared to the similar composition using only EVA.

In conclusion, the ethylene/octene copolymers improve the performance of the compositions, in particular based on synthetic resins, in particular hydrogenated resins, and offer a new range of products with modified properties. These interesting results are not explained in line with the prior art and were unexpected.

EVA (at 28% VA) and copolymers of ethylene octene may also act in synergy and provide the product with tearing properties and interesting mechanical properties compared to the products of the prior art.

The ethylene octene copolymers used above constitute a particular case of macromolecular components of the class of copolymers of two or more monomers taken from the group comprising ethylene and alpha olefins. For the application described, preference is given to low crystallinity or even amorphous components. They are advantageously obtained by coordinative polymerization with a Zigler Natta catalyst, for example a metallocene catalyst. The invention extends to the use of copolymers of two or even three or more units taken from alpha-olefins and ethylene, wherein all the monomers may be different from ethylene, and at least one monomer may have, for example, at least 4 or at least 5 carbons.

The invention claimed is:

1. An adhesive composition for strip-free hair removal comprising at least 50% by weight of a cyclopentadiene resin and between 5% and 15% by weight of an ethylene/octene copolymer for modulating the strength properties or the adhesive properties of the composition, and wherein the composition does not contain ethylene vinyl acetate copolymer.

2. The adhesive composition according to claim 1, wherein the cyclopentadiene resin is present at at least 60% by weight.

3. The adhesive composition according to claim 1, wherein the ethylene/octene copolymer is a copolymer obtained by coordination polymerization.

4. The adhesive composition according to claim 3, wherein the coordination polymerization is catalyzed by a metallocene.

5. The adhesive composition according to claim 1, wherein the ethylene/octene copolymer is characterized by a melt index of more than 100 g/10 min with 2.16 kg at 190° C., or more than 250 g/10 min with 2.16 kg at 190° C.

6. The adhesive composition according to claim 1, wherein the ethylene/octene copolymer is characterized by a melt index of less than 800 g/10 min with 2.16 kg at 190° C.

7. The adhesive composition according to claim 1, wherein the ethylene/octene copolymer is characterized by a density of between 0.86 and 0.91 g/cm$^3$.

8. An adhesive composition for strip-free hair removal comprising at least 50% by weight of a cyclopentadiene resin and between 1% and 18% by weight of a combination of an ethylene/octene copolymer and an ethylene vinyl acetate copolymer, wherein the ethylene/octene copolymer is for modulating the mechanical strength properties or the adhesive properties of the composition.

9. The adhesive composition according to claim 8, wherein the composition comprises between 5% and 15% by weight of the combination of the ethylene/octene copolymer and the ethylene vinyl acetate copolymer.

10. The adhesive composition according to claim 9, wherein the composition comprises at least 60% by weight of the cyclopentadiene resin.

11. The adhesive composition according to claim 8, wherein the composition comprises at least 60% by weight of the cyclopentadiene resin.

12. A depilatory method comprising heating the adhesive composition of claim 1 between 50° C. and 75° C. to form a warm paste, applying a layer of the warm paste to skin in need of depilation, cooling the layer of the warm paste to form a solidified layer, and peeling the solidified layer off the skin in the opposite direction of the growth of the hair.

13. The depilatory method according to claim 12, wherein the cyclopentadiene resin is present in a concentration of at least 60% by weight.

14. A depilatory method comprising heating the adhesive composition of claim 8 between 50° C. and 75° C. to form a warm paste, applying a layer of the warm paste to skin in need of depilation, cooling the layer of the warm paste to form a solidified layer, and peeling the solidified layer off the skin in the opposite direction of the growth of the hair.

* * * * *